(12) United States Patent
Olson

(10) Patent No.: US 6,716,391 B1
(45) Date of Patent: Apr. 6, 2004

(54) AUTOMATED CHEMILUMINESCENCE ANALYZER

(75) Inventor: Don C. Olson, Gig Harbor, WA (US)

(73) Assignee: Global FIA, Inc., Gig Harbor, WA (US)

( * ) Notice: Subject to any disclaimer, the term of this patent is extended or adjusted under 35 U.S.C. 154(b) by 0 days.

(21) Appl. No.: 10/249,187

(22) Filed: Mar. 20, 2003

(51) Int. Cl.$^7$ ................................................ G01N 21/64
(52) U.S. Cl. ..................................... 422/52; 250/361 C
(58) Field of Search .............................. 422/52, 81–82; 250/361 C; 436/52–53, 172

(56) References Cited

U.S. PATENT DOCUMENTS

| 4,193,963 A | | 3/1980 | Bruening et al. ............... 422/52 |
| 4,634,574 A | | 1/1987 | Spurlin et al. ................. 422/52 |
| 4,816,226 A | * | 3/1989 | Jordan et al. .................. 422/81 |
| 5,422,075 A | | 6/1995 | Saito et al. .................... 422/52 |
| 5,494,824 A | * | 2/1996 | Tanaka et al. ............. 435/288.7 |
| 5,614,417 A | | 3/1997 | Kubala et al. ............... 436/120 |
| 5,668,014 A | * | 9/1997 | Aoki et al. .................. 436/110 |
| 6,304,327 B1 | | 10/2001 | Campbell et al. ........... 356/437 |
| 6,332,049 B1 | | 12/2001 | Dasgupta ...................... 385/12 |
| 6,613,581 B1 | * | 9/2003 | Wada et al. ................. 436/518 |
| 2003/0095897 A1 | * | 5/2003 | Grate et al. ................. 422/186 |

* cited by examiner

Primary Examiner—Jeffrey R. Snay
(74) Attorney, Agent, or Firm—Reginald F. Roberts, Jr.

(57) ABSTRACT

An automated chemiluminescence analyzer. A multiport selection valve has a common aspiration port for carrier solvent, sample, and reagent. A bi-directional pump is connected to the selection valve. A chemiluminescence cell is positioned between the selection valve and a T-block. One end of the cell is connected to the common port of the selection valve, and the other end is connected to the T-block. The T-block has a port connected to the pump, another port which communicates with the detector, and a third port connected to the other end of the cell. This unique arrangement enables the chemiluminescence cell to function as a chemical reactor, thus eliminating any delay between initiation and detection of emitted radiation, so that very rapid reactions can be viewed and high sensitivity attained.

4 Claims, 3 Drawing Sheets

AUTOMATED CHEMILUMINESCENCE ANALYZER

BACKGROUND OF INVENTION

The present invention relates to instrumental chemical analysis. More particularly, the invention relates to instrumental chemiluminescence analysis.

Chemiluminescence (CL) is the generation of light from chemical reactions. CL processes have attracted mankind's attention for centuries. Aristotle wrote the first known report on the phenomenon when he noted weak light emitted by dead fish and fungi. The term chemiluminescence was first defined by Wiedemann in 1888 as light emitted from chemical reactions.

Many CL reactions are now well known. Early studies of CL focused primarily on the chemistry and mechanisms of CL reactions. In the early 1960's analytical applications of CL reactions began to appear in the literature. Since then, CL analytical methods have grown substantially due to the advantages of low detection limits, wide linear dynamic ranges, and fast response.

The early analytical applications involved manual techniques for mixing reagent and sample, and measuring the light emitted. In 1975 Ruzicka and Hansen introduced Flow Injection Analysis (FIA), which provided a new tool for performing CL analyses.

With FIA, reagent and sample can be automatically mixed rapidly and reproducibly in a flowing stream in close proximity to the CL detector. Flow cell designs which caused reagent and sample to merge directly in front of the detector allowed rapid CL chemistry to be viewed. This automation made CL an even more attractive analytical technique.

In 1990 Ruzicka and Marshall introduced Sequential Injection Analysis (SIA). SIA is a variant of FIA which offers some important advantages. Whereas with FIA the sample is injected into a flowing carrier stream, with SIA adjacent sample and reagent zones are aspirated into a holding coil, and then the flow is reversed to transport the zones to the detector. Mixing and chemistry between the zones occurs during transport. SIA can be performed with simpler hardware and uses much less reagent compared to FIA.

In 1994 Tucker et al. applied SIA to CL analysis. A schematic of the system is shown in FIG. 1, and is generally designated by the numeral 2. The system 2 comprises a carrier solvent 4, a syringe pump 6, a holding coil 8, a multiport selection valve 10, a chemiluminescence flow cell 12, sample 14, reagent 76, and a detector 18. The technique provided the advantage of consumption of much less reagent 16, and generated less waste. However, since mixing and chemical reaction are initiated as sample 14/reagent 16 zones are aspirated into the holding coil 8, and continue as the flow is reversed and the reaction zone is transported to the detector 18, there is a time delay before the light-emitting zone reaches the flow cell 12 and detector 18. This delay is a disadvantage of SIA in its conventional prior-art configuration when used with rapid CL reactions.

In 1999 Dasgupta reported a liquid-core waveguide (LCW) cell for CL by FIA, and later was issued a patent on the invention. Sample and reagent are merged at the entrance of the tubular LCW. The LCW acts both as a mixing/reaction cell and a light collector. An LCW has the property that light generated within Its lumen is efficiently transmitted to both ends of the LCW. The light arriving at either end of the LCW is then measured with a suitable detector. FIA with an LCW cell has two major advantages. First, since mixing of sample and reagent occurs primarily within the LCW, CL from very fast reactions can be detected. Second, because the LCW effectively collects and transmits most of the CL emission, a high-detection sensitivity can be achieved.

SUMMARY OF INVENTION

In general, the present invention provides an automated chemiluminescence analyzer. The analyzer comprises (a) a multiport selection valve, (b) a bi-directional pump, (c) a flow-through chemiluminescence cell, (d) a multiport block, and (e) a detector. The multiport valve includes a common aspiration port for carrier solvent, sample, and reagent; inlet ports for sample and reagent; and an outlet port. The pump is connected to the selection valve. The chemiluminescence cell is disposed between the selection valve and the multiport block. A first end of the cell is connected to the common port of the selection valve, and a second end is connected to the multiport block. The multiport block has a first port connected to the pump, a second port which communicates with the detector, and a third port connected to the second end of the cell. The outlet port of the selection valve is constructed and arranged for discharging and flushing the cell with solvent by reversing the direction of flow through the pump.

DETAILED DESCRIPTION

Figure 2:
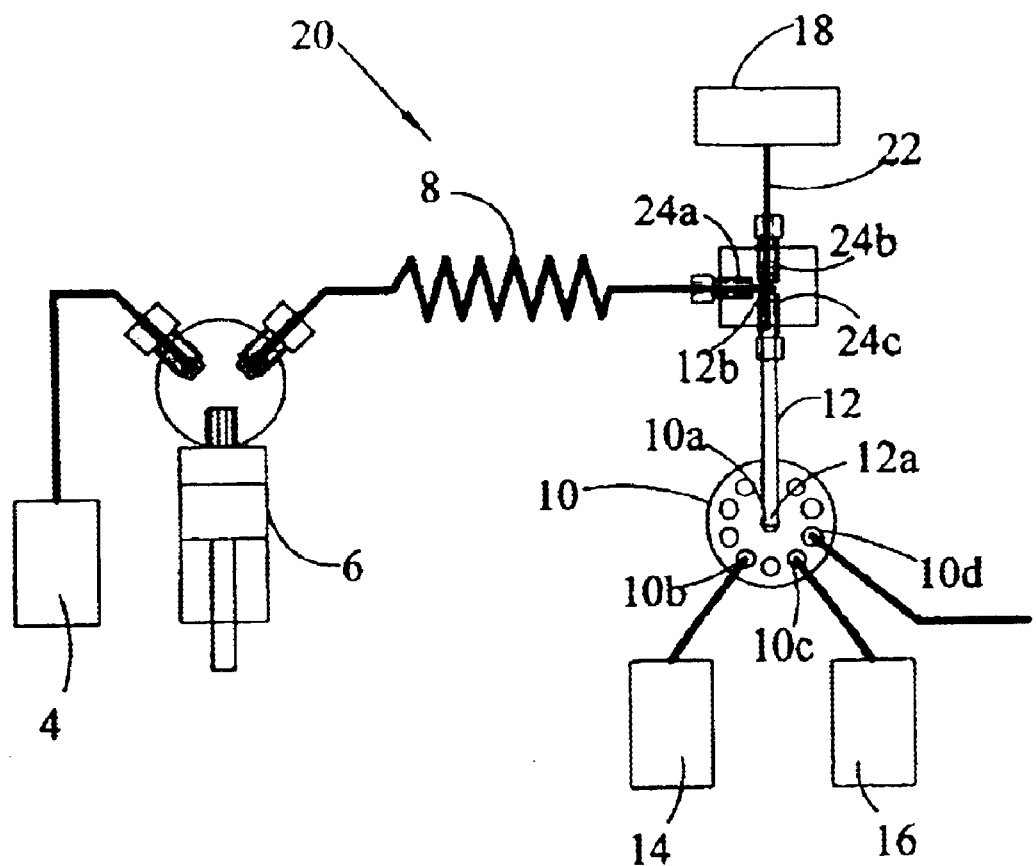
FIG. 2 is a schematic representation of an automated chemiluminescence analyzer, made in accordance with the principles of the present invention.

More specifically, reference is made to FIG. 2, in which is shown an automated chemiluminescence analyzer, made in accordance with the principles of the present invention, and generally designated by the numeral 20.

The chemiluminescence analyzer 20 comprises (a) a multiport selection valve 10, (b) a bidirectional pump 6, (c) a flow-through chemiluminescence cell 12, (d) a T-block 24, (e) a detector 18, and (f) a holding coil 8.

The multiport valve 10 includes a common aspiration port 10a for sample 14 and reagent 16, inlet ports 10b and 10c for sample 14 and reagent 16, respectively; and an outlet port 10d.

The pump 6 is connected to the selection valve 10 through the holding coil 8.

The chemiluminescence cell 12 is beneficially disposed between the selection valve 10 and the T-block 24. A first end 12a of the cell 12 is connected to the common port 10a of the selection valve 10, and a second end 12b is connected to the T-block 24. The T-block 24 has a first port 24a connected to the pump 6 through the holding coil 8, a second port 24b which communicates with the detector 18, and a third port 24c connected to the second end 12b of the cell 12.

Figure 1:
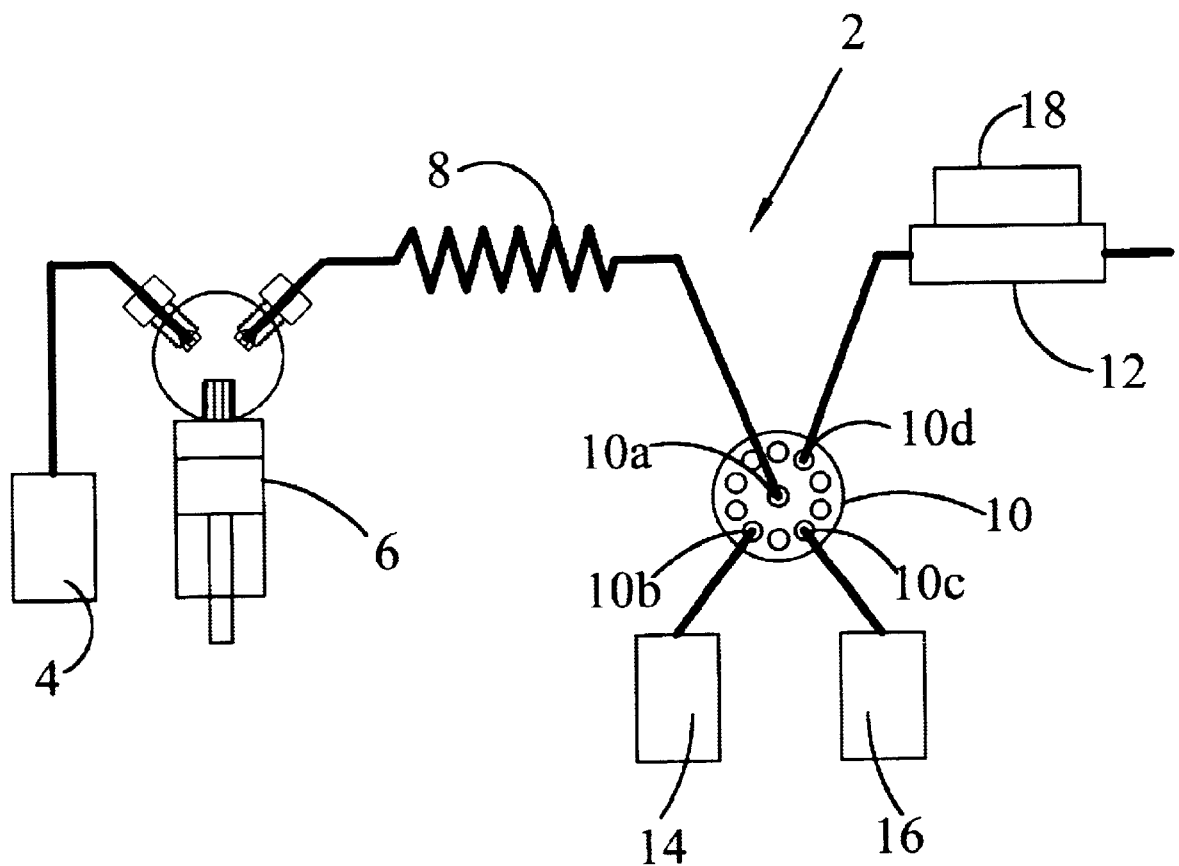
FIG. 1 is a schematic representation of a prior-art chemiluminescence analyzer.

This novel arrangement of the selection valve 10, chemiluminescence cell 12, and detector 18 is crucial to the inherent advantages of the present invention over the prior art. As shown in FIG. 1, in standard SIA, mixing and chemical reaction are initiated as sample 14/reagent 16 zones are aspirated into the holding coil 8, and continue as the flow is reversed and the reaction zone is transported to the detector 18. This conventional arrangement causes and necessitates a time delay before the light-emitting zone reaches the flow cell 12 and the detector 18. This delay is a serious disadvantage of SIA when used with rapid CL reactions.

By connecting the first end 12a of the CL flow cell 12 directly to the common aspiration port 10a of the selection valve 10 and the second end 12b to the third port 24c of the T-block 24, as shown in FIG. 2, mixing and chemical reaction of the sample 14 and the reagent 16 are initiated at the entrance 12a of the cell 12, and there is no delay between initiation of CL and detection of the emitted light. Thus, very rapid reactions can be viewed and high sensitivity attained in CL analyses. By aspirating a plurality of alternating zones of sample 14 and reagent 16 into the cell 12, stopping the flow, and collecting and integrating the light generated, even higher sensitivity can be achieved. The number of alternating zones of sample 14 and reagent 16 can vary, from one pair to several pair. The final step is to reverse flow and flush the cell 12 with solvent through a waste outlet port 10d of the selection valve 10, to prepare the chemiluminescence analyzer 20 for the next analysis. Cycle time is short, generally from about five to about sixty seconds.

The function of the holding coil 8 in the chemiluminescence analyzer 20 of the present invention is simply to serve as a barrier between the cell 12 and the pump 6, so that if any of the reaction mixture passes through the cell 12 due to aspiration of too large a volume of sample 14/reagent 16 zones, it will not reach the pump 6. Thus, its purpose differs from the prior-art chemical analyzers in that the holding coil 8 does not serve to "hold" and mix the sample/reagent zones before sending them to the detector 18.

Preferably, the cell 12 is an LCW cell, in order to provide maximum sensitivity, and the second port 24b of the T-block 24 is optically connected to the detector 18 by an optical fiber 22, or some other suitable interface, such as a window. If an optical fiber is used it is preferable, but not necessary, that it extend into the flow-cell channel in order to increase the collection of light.

The present invention will now be illustrated by the following example, which is not to be construed as in any sense limiting the scope of the invention.

EXAMPLE

The sample 14 was a water solution of $2.61 \times 10^{-10}$ molar (M) adenosine triphosphate (ATP). The reagent 16 was Enliten®, a registered trademark of Promega Corporation, a mixture of luciferin and luciferase (L/L) in buffer with stabilizers, purchased from Promega Corp., 2800 Woods Hollow Road, Madison, Wis. 57711. The ATP L/L reaction is a well-known chemiluminescence reaction that is used in a number of different analytical applications. The cell 12 was an LCW cell made of an amorphous fluoropolymer which is a copolymer of tetrafluoroethylene and perfluoro-2,2-dimethyl-1,3-dioxane, marketed under the registered trademark TEFLON AF® by E. I. Dupont de Nemours, a corporation of Wilmington, Del. The cell 12 had an internal diameter (ID) of seven one-hundredths of an inch (in), and a length of eight centimeters (cm). The detector 18 was a photomultiplier tube (PMT). A thin frit having a pore size of from about ten to about twenty microns was placed at the first end 12a of the cell 12, to enhance mixing of the sample 14 and the reagent 16.

To prepare the system for a run or series of runs, the lines from the selection valve 10 to the pump are flushed and filled with solvent. This is accomplished by aspirating a volume of solvent from carrier solvent 4 through the inlet port of the three-way syringe valve into the syringe, then dispensing the solvent through the outlet port 10d of the three-way syringe valve to the LCW and to waste through outlet port 10d of selection valve 10. In a first step of a run, a volume of flush solvent is aspirated into the syringe in the same manner as described above. This volume of flush solvent is used at the end of the run. In a second step, two-hundred microliters of the ATP sample 14 were aspirated into the cell 12. This was followed in rapid succession by ten microliters of the reagent 16, then twenty-five microliters of ATP, for a total of six times. All aspirations were performed at a rate of ten milliliters per minute (ml/min). After a waiting period of thirty seconds (sec), the flow was reversed and the cell 12 flushed with solvent 4 to waste through an outlet port 10d of the selection valve 10.

Figure 3:
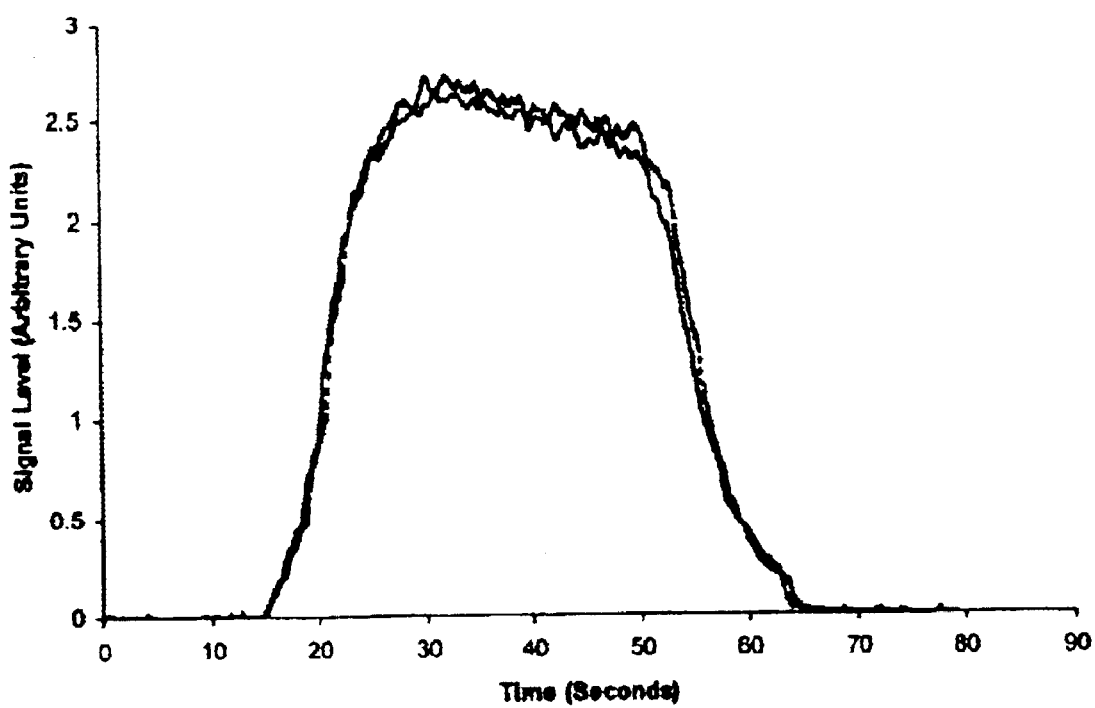
FIG. 3 is a graphical representation showing detector response as a function of elapsed time, for a CL analysis utilizing the automated chemiluminescence analyzer of FIG. 2.

FIG. 3 shows duplicate peak profiles of the detected radiation. The initial ascending branch of the curve is generated by light emitted during the aspiration-mixing state. At the peak of the curve aspiration and mixing are complete, flow has stopped, and a gradual decay in light generated is observed as the ATP is depleted by the chemical reaction. At the end of this stage—stopped flow—the flow is reversed and a rapid drop in signal is observed as the reaction mixture was flushed from the cell 12. Either peak height or peak area of the signal peak may be used for analytical applications.

While certain embodiments and details have been used to illustrate the present invention, it will be apparent to those skilled in the art that many modifications are possible without departing from the spirit and scope of the invention.

I claim:

1. An automated chemiluminescence analyzer, comprising:
   (a) a multiport selection valve;
   (b) a bidirectional pump;
   (c) a flow-through chemiluminescence cell;
   (d) a multiport block; and
   (e) a detector;
   the multiport selection valve including a common aspiration port for carrier solvent, sample, and reagent; inlet ports for sample and reagent; and an outlet port; the pump being connected to the selection valve; the chemiluminescence cell being disposed between the selection valve and the multiport block, a first end of the cell being connected to the common port of the selection valve, and a second end being connected to the multiport block; the multiport block having a first port connected to the pump, a second port which communicates with the detector, and a third port connected to the second end of the chemiluminescence cell; the outlet port of the selection valve being constructed and arranged for discharging and flushng the cell with solvent by reversing the direction of flow through the pump.

2. The chemiluminescence analyzer of claim 1, wherein the second port of the multiport block is optically connected to the detector by an optical fiber or other suitable inteface.

3. The chemiluminescence analyzer of claim 1, further comprising:
   (f) a holding coil disposed between the pump and the first port of the T-block, to act as a barrier between the cell and the pump, and thereby prevent any excess of sample and/or reagent aspirated into the cell from being returned to the pump.

4. The chemiluminescence analyzer of claim 1, wherein the multiport block is a T-block.

* * * * *